United States Patent [19]
Riley

[11] Patent Number: 6,133,837
[45] Date of Patent: Oct. 17, 2000

[54] PATIENT POSITION SYSTEM AND METHOD FOR A SUPPORT SURFACE

[75] Inventor: Carl William Riley, Milan, Ind.

[73] Assignee: Hill-Rom, Inc., Batesville, Ind.

[21] Appl. No.: 09/262,811

[22] Filed: Mar. 5, 1999

[51] Int. Cl.⁷ .............................................. G08B 23/00
[52] U.S. Cl. ...................... 340/573.1; 340/524; 340/666; 73/1.79; 73/65.01
[58] Field of Search ........................... 340/573.1, 825.06, 340/825.07, 573.4, 825.36, 666, 524; 73/1.13, 1.15, 1.79, 65.01, 65.09, 781, 152.5

[56] References Cited

U.S. PATENT DOCUMENTS

| | | | |
|---|---|---|---|
| 3,533,095 | 10/1970 | Collins | 340/573.1 |
| 3,752,144 | 8/1973 | Weigle, Jr. | 600/587 |
| 3,890,958 | 6/1975 | Fister et al. | 128/774 |
| 4,175,263 | 11/1979 | Triplett et al. | 340/573.1 |
| 4,320,766 | 3/1982 | Alihanka et al. | 128/671 |
| 4,474,185 | 10/1984 | Diamond | 128/722 |
| 4,539,560 | 9/1985 | Fleck et al. | 340/573.1 |
| 4,633,237 | 12/1986 | Tucknott et al. | 340/573.1 |
| 4,796,013 | 1/1989 | Yasuda et al. | 340/562 |
| 4,858,620 | 8/1989 | Sugarman et al. | 128/774 |
| 4,934,468 | 6/1990 | Koerber, Sr. et al. | 177/144 |
| 4,951,032 | 8/1990 | Langsam | 340/686.1 |
| 4,953,244 | 9/1990 | Koerber, Sr. et al. | 177/144 |
| 5,140,309 | 8/1992 | Gusakov | 340/573.1 |
| 5,144,284 | 9/1992 | Hammett | 340/573.1 |
| 5,170,364 | 12/1992 | Gross et al. | 364/558 |
| 5,184,112 | 2/1993 | Gusakov | 340/573.1 |
| 5,235,319 | 8/1993 | Hill et al. | 340/573.1 |
| 5,253,656 | 10/1993 | Rincoe et al. | 128/782 |
| 5,276,432 | 1/1994 | Travis | 340/573.1 |
| 5,353,012 | 10/1994 | Barham et al. | 340/573.1 |
| 5,355,012 | 10/1994 | Yamaguchi et al. | 257/409 |
| 5,393,935 | 2/1995 | Hasty et al. | 177/45 |
| 5,410,297 | 4/1995 | Joseph et al. | 340/573.1 |
| 5,446,391 | 8/1995 | Aoki et al. | 324/661 |
| 5,448,996 | 9/1995 | Bellin et al. | 128/671 |
| 5,459,452 | 10/1995 | DePonte | 340/604 |
| 5,471,198 | 11/1995 | Newham | 340/573.1 |
| 5,479,939 | 1/1996 | Ogino | 128/782 |
| 5,543,777 | 8/1996 | Vane et al. | 340/514 |
| 5,602,734 | 2/1997 | Kithil | 364/424.055 |
| 5,633,627 | 5/1997 | Newham | 340/573.1 |
| 5,654,694 | 8/1997 | Newham | 340/573.1 |
| 5,697,366 | 12/1997 | Kimball et al. | 128/632 |
| 5,699,038 | 12/1997 | Ulrich et al. | 340/573.1 |
| 5,791,344 | 8/1998 | Schulman et al. | 128/635 |
| 5,800,480 | 9/1998 | Augustine et al. | 607/96 |
| 5,802,479 | 9/1998 | Kithil et al. | 701/45 |
| 5,808,522 | 9/1998 | Wiley et al. | 340/573.1 |
| 5,808,552 | 9/1998 | Wiley et al. | 340/573.1 |
| 5,844,488 | 12/1998 | Musick | 340/573.1 |
| 5,861,582 | 1/1999 | Flanagan et al. | 177/144 |
| 5,993,400 | 11/1999 | Rincoe et al. | 600/595 |

FOREIGN PATENT DOCUMENTS

| | | |
|---|---|---|
| 0 441 381 A1 | 8/1991 | European Pat. Off. . |
| WO 89/02635 | 3/1989 | WIPO . |

*Primary Examiner*—Daniel J. Wu
*Assistant Examiner*—Taon Pham
*Attorney, Agent, or Firm*—Barnes & Thornburg

[57] ABSTRACT

A system for determining the location of a patient on a support. The system includes a first and second sensor coupled to a patient's support surface and being at least laterally spaced. A first load signal from the first sensor has a first sensitivity greater than a second sensitivity of a second load signal from the second sensor. A determination circuit receives a first and second load signals and provides an indication of the location of the patient on the support surface from a comparison of the sum of the load signals to a selected value.

43 Claims, 5 Drawing Sheets

PATIENT POSITION SYSTEM AND METHOD FOR A SUPPORT SURFACE

BACKGROUND AND SUMMARY OF THE INVENTION

The present invention relates generally to a method and apparatus of determined location of a patient on a support surface and more specifically, to its application to an exit alarm system.

The patient exit alarm systems vary from a very simple sensor switch which determines when the patient is not in the center of the bed to various sophisticated systems which determines the center of gravity of the weight from various sensors about the periphery of the support surface. While the simple sensor switch is inexpensive, the calculation of the center of gravity requires a microprocessor or other digital computing device and therefore, is relatively expensive.

A system in between the two systems just described, includes four corner sensors and a center sensor is illustrated in FIG. 10. The change in value of all of the five sensors are determined and various combinations of these changes are used to determine whether the patient has exited the bed or whether the patient is getting ready to exit the bed. While the exit determination is made on the change of the total weight, or changes in the weight of the center sensor in combination with the changes of the other sensors, the prediction of an exit is determined from changes in the center sensor with also large changes in one of the other four sensors. Such a system is described in U.S. patent application Ser. No. 09/031,749 filed Feb. 24, 1998 to inventor Tom Scott.

Systems using a calculation of the center of gravity using signals from a plurality sensor or load cells generally assumes that all the sensors are identical and calibrated to the same parameters. Also, their installation or positioned relative to each other affects its accuracy. The systems which make determinations of changes of signals from a sensor minimizes the calibration of positioning error introduced in the center of gravity calculation systems.

The present invention is a bed system for determining the location of a patient on a support surface. The system includes a first and second sensor coupled to the patient support surface and being at least laterally spaced. A first load signal from the first sensor has a first weight greater than a second weight of a second load signal from the second sensor. A determination circuit receives a first and second load signals and provides an indication of the location of the patient on the support surface from a comparison of the sum of the load signals to a selected value.

The first and second sensors may also be longitudinally spaced. If a third sensor is used, it is longitudinally spaced from the first sensor and its load signal has a third weight less than the first weight. If a fourth sensor is provided, it is longitudinally spaced from the second sensor and laterally spaced from the third sensor and its load signal has a fourth weight which is less than the first weight. The third and fourth weights may be greater than or equal to the second weight and may be equal to each other or different from each other.

The signal processing circuit is provided for setting the weight of the loads. In an analog system, the signal processing or weight setting circuit includes impedance for setting the weight of the load signals. In a digital system, the signal processing is a programmable signal processor and the weights are set by programming. Also, the determination circuit may be part of the digital or programmable signal processor.

The selected value for the comparison may be the sum taken when the patient is substantially centered on the support surface. The selected value may also be selected based on the weight of the patient or based on the range of weight in which the weight of the patient lies. The determination circuit may also provide an indication of location of the patient on the support surface by comparing the sum of the load signals to a plurality of selected values. The determination circuit provides an indication of location of the patient on the support surface when the comparison of the sum of the load signals to the selected value is greater than a selected amount. An alarm indication may also be provided when the comparison is greater than the selected amount or when the location is determined that the patient is adjacent the edge of the support surface.

A method of the present invention for determining the location of the patient on the support surface have load sensors, the method comprises weighting a first load signal of the first sensor to a first weight and weighting the second load signal of the second sensor to a second weight less than the first weight. The weighed load signals are compared to a selected value. The location of the patient on the support surface is determined from the results of the comparison.

The selected value is set to the sum taken when the patient is substantially centered. Alternatively, the selected value may be set based on the weight of the patient or on the range of weight in which the weight of the patient lies. The location of the patient can also be determined from comparing the sum of the load signals to a plurality of selected values. Also, the location can be determined when the comparison of the sum of the loaded values to the selected value is greater than a selected amount. An alarm indication can be provided when the location of the patient on the support surface is adjacent the edge of the support surface. If multiple sensors are provided, they are also weighted to a weight less than the weight of the first load signal.

Other advantages and novel features of the present invention will become apparent from the following detailed description of the invention when considered in conjunction with the accompanying drawings.

DETAILED DESCRIPTION OF THE PREFERRED EMBODIMENTS

Figure 1:
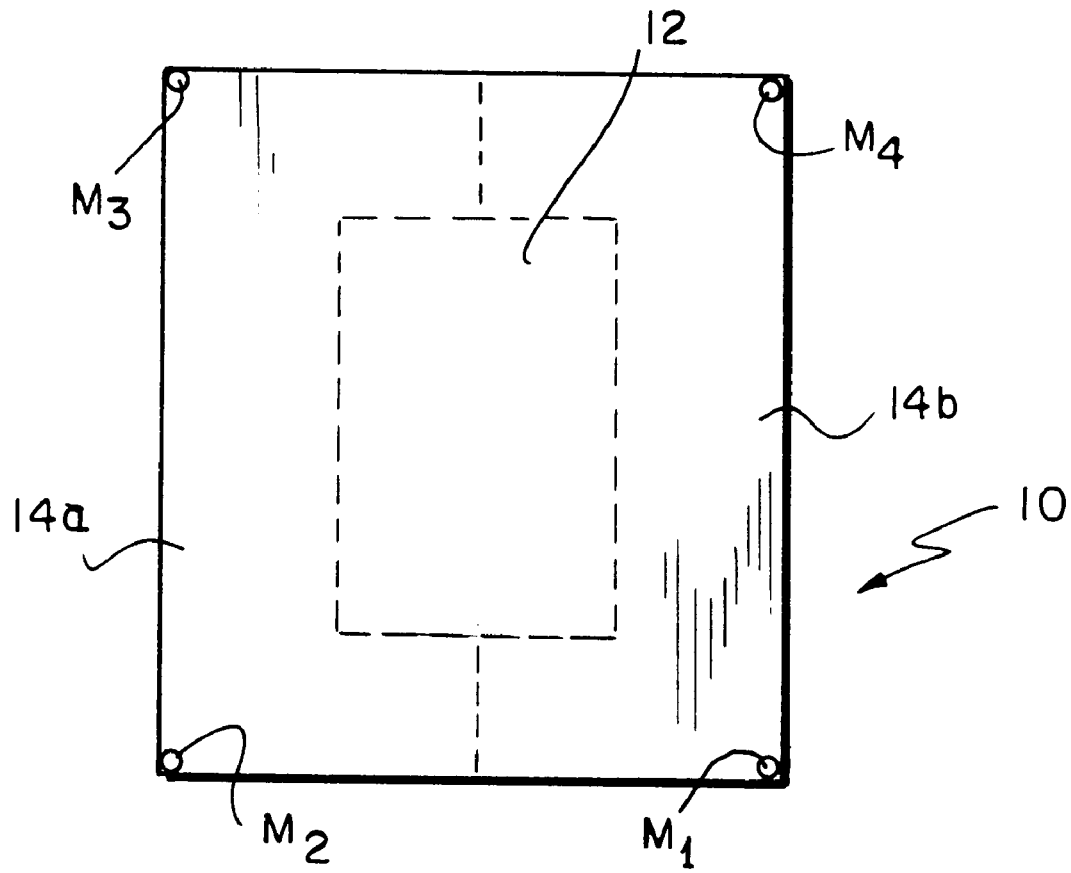
FIG. 1 is a plan schematic view of a support surface with four load sensors.
Figure 2:
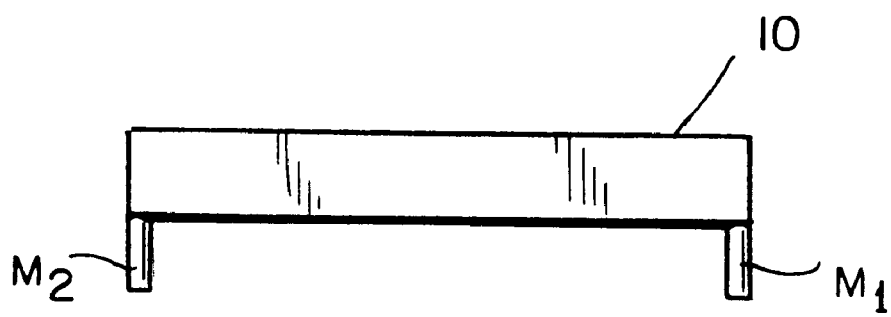
FIG. 2 is a side view of the system of FIG. 1.

A patient support surface 10, as shown in FIG. 1, is supported on four load cells M1, M2, M3 and M4. The four load cells may be load cells coupled directly to the support surface 14 or may be part of a weigh frame which are already available in a bed or other support surface for a patient for example a chair. Load cells are typically coupled between a base frame of a bed and the weigh frame. Other frames, such as an intermediate frame, and a retracting frame may also be coupled between the weigh frame and a patient support deck which forms the support surface 14. Therefore, when it is stated that the sensors are coupled to the support surface, the sensors may be either directly coupled to the support surface or coupled to one of the frames of the bed which support the support surface. The load cells M1–M4 may be resistive, capacitive, piezoelectric or other load cells whose output signals varies with the load applied to the load cells from the support surface 14.

Figure 10:
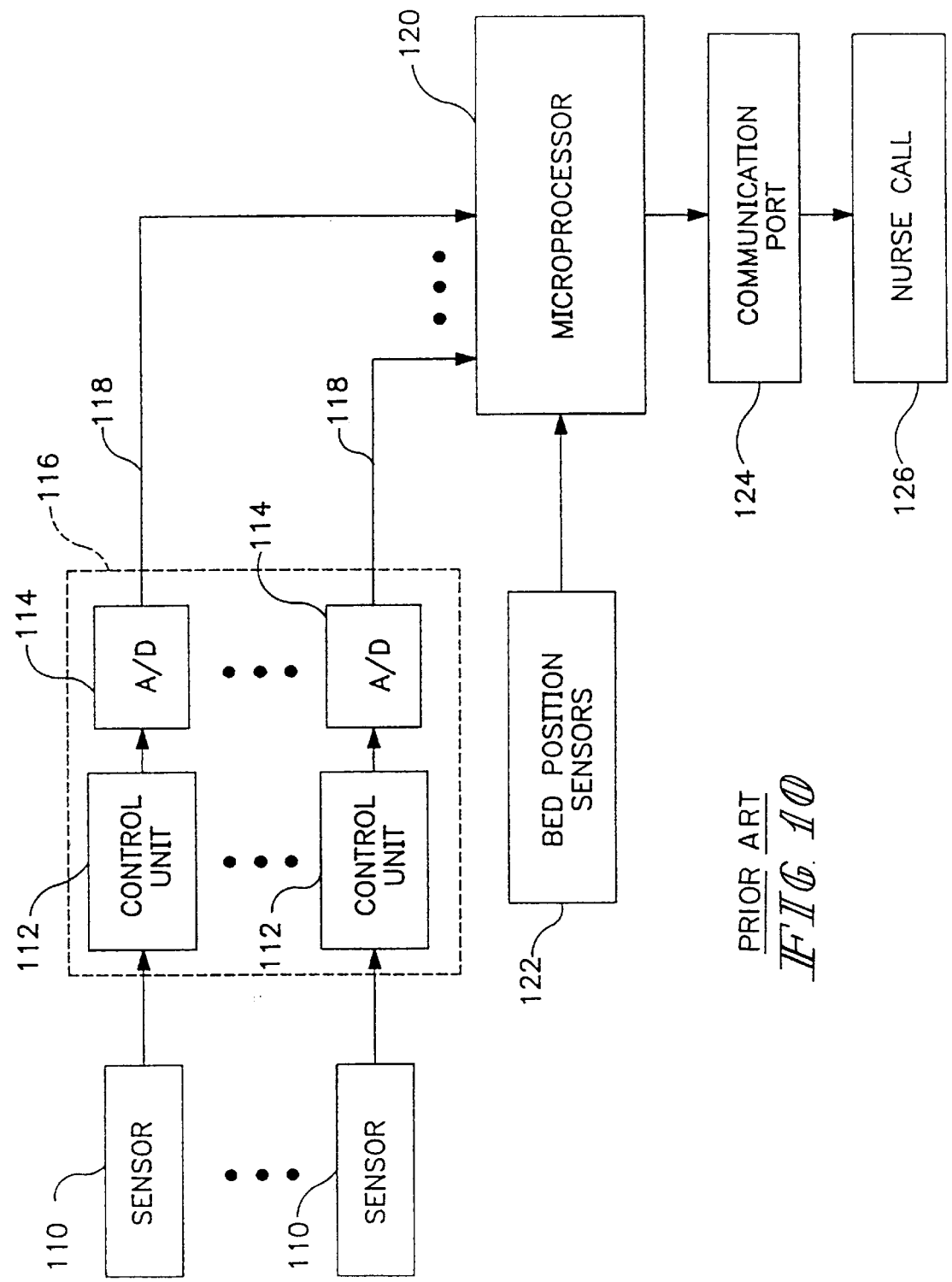
FIG. 10 is a schematic of a digital sensing system of the prior art.

As previously discussed, the prior art systems which provide an indication of the location of the patient on the support surface, either by calculating the center of gravity or by indicating or predicting an exit, monitors each of the signals from the load cells M1–M4 individually. The digital system of FIG. 10 includes sensors 110, coupled to control units 112 and A/D converters 114 of control board 116. A microprocessor 120 receives the digital signals from control board 116 and bed position sensor 122 and after signal processing provides an output through communication port 124 to for example, nurses station 126. For further details, reference is made to the Scott patent application which is incorporated herein by reference.

The present invention attempts to minimize the amount of equipment calculation and source of error by recognizing that as the patient moves about the support surface 10, that the total weight does not change even though the load received by the individual sensors change relatively to each other. In the simplest case and referring to FIG. 1, as a patient moves from the center zone 12 towards the exteriors zone 14 of the support surface 10, for example, to the right in FIG. 1, the value of the signals of load sensors M1 and M4 will increase and those of M2 and M3 will decrease. The amount of increase of M1 and M4 equals the amount of decrease of M2 and M3 since the total weight or load sensed, is constant as long as the patient is on the support surface. Thus, the prior art system monitored the individual sensors to make a determination of where the patient is on the surface even for a simple determination, whether they are in the zone 12 or zone 14.

The system and method of the present invention in the simplest possible manner, weighs signals from the individual sensors such that the total weighted weight changes as the patient moves about the support surface 10. This allows the use of a minimal number of analog elements as well as simple minimal processing in a microcomputer. If the output from sensor M2 is weighted to have a greater weight or sensitivity compared to the other sensors M1, M3 or M4, the total of the four values from the four sensors will increase or decrease, depending upon the position of the patient relative to the sensor M2.

As a first example, lets assume that the weighting or sensitivity of sensors M1, M3 and M4 equal to each other and are half the sensitivity of sensor M2. As the occupant moves to the right of FIG. 1, the increase in sensor M4 will be equal to the decrease in sensor M3. The increase in sensor M1 will be half the decrease of that of sensor M2 since it is half the sensitivity or weight. Thus, the total weight of all four sensor load signals will be less than the total weight when the occupant is in the center since M2 has decreased at twice the rate that M1 has increased. For example, assume that the weight shift to the right is 20 lbs. The actual weight change at sensors $M_1$ and $M_4$ each increase by 10 lbs. and the actual weight at sensors $M_2$ and $M_3$ each decrease by 10 lbs. Because of the sensitivity, the "weighted" signals for sensors $M_1$ and $M_4$ each increase by 5 lbs. and for sensors $M_2$ and $M_3$ will decrease by 10 lbs. and 5 lbs. respectively. Thus, the total weighted weight will decrease by 5 lbs.

If the occupant had moved left, then M2 would increase at twice the rate that M1 would decrease, and therefore the sum would be greater than the sum when the occupant was in the center of the support surface 10. The same would be true as applicant moves up or down. In that case, M1 and M4 would cancel each other while M2 will increase or decrease at twice the rate of M3.

For increased accuracy, all sensors should have unequal weights or sensitivity. Preferably a pair of diagonal sensors have the greatest difference in weight or sensitivity. Also greater accuracy is achieved with more sensors.

By comparing the total of the sensors' signals against the sum of the sensors' signal when the patient is in the center position, would give an indication of the position of the patient on the support surface 10. If the number is negative, then the patient is moving away from the heavy weighted sensor M2 and if it is positive, the patient is moving towards the sensor M2. By comparing the amount of change to another amount, will indicate whether the patient is in zone 12 or in zone 14. The difference of the center sum to the present sum may also be compared against multivalues to determine multiple zones of the locations of the patient with respect to a center zone.

If determination is only to be made whether there is a center zone 12 or in one or more outer zones 14, the absolute value of change can be used since the exact location may not be desired. This would be used to provide an exit alarm and an anticipation of an exit.

Figure 3:
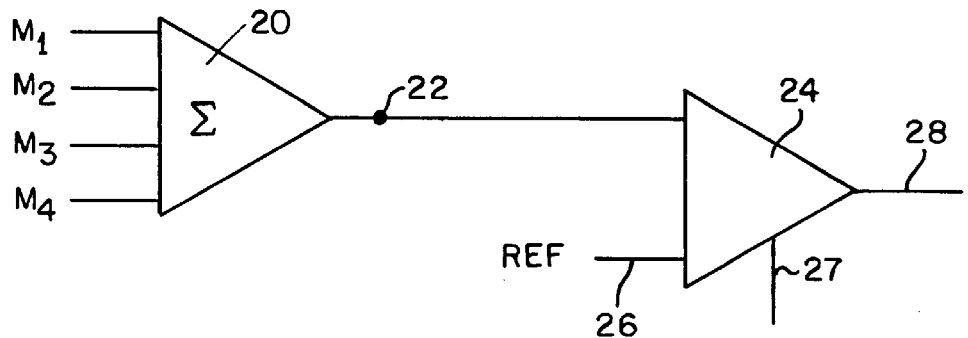
FIG. 3 is a schematic of an analog circuit incorporating the principles of the present invention.

FIG. 3 is an example of an analog circuit which is capable of making a determination of whether the patient is in zone 14a or not in zone 14a. The four analog signals are provided to a summary amplifier 20. The output 22 is provided as one input to a comparator 24. The other input is a reference or threshold 26 which defines the zone or boundary. The comparator 24 also has an offset input 27, which is a reference weight and is a function of the weight of the patient. The difference between the signal 22 and 26 including offset 27 are provided at the output 28 of the comparator 24. Alternatively, the offset input 27 may define the boundary or threshold and the reference input 26 may be the reference weight. The signals M1–M4 are weighted signals such that variation of the movement of the occupant on the support surface produces different outputs 22 of the summing amplifier 20.

The offset input 27 may be a number selected based on the actual weight of the occupant taking into account the weighting factors of the sensors. Instead of being an actual value, it may be one of three preset values, depending upon a range of weight in which the weight of the patient lies. These selections or values may be selected manually by a nurse or care giver or provided from another system on the bed. For example, it may be light, average or heavy.

Once the difference between the sum 22 and the offset signal 27 exceed the boundary signal 26, the output signal 28 changes polarity. The change of polarity indicates that the occupant is in zone 14a. Signal 28 may be an alarm signal locally or remotely or may be an actual value. The example of FIG. 3 is for a single zone 14a and may be appropriate where the other sides of zone 14b are obstructed. This would be the case if the zone 14b was against a wall or was the side or back of a chair.

Figure 4:
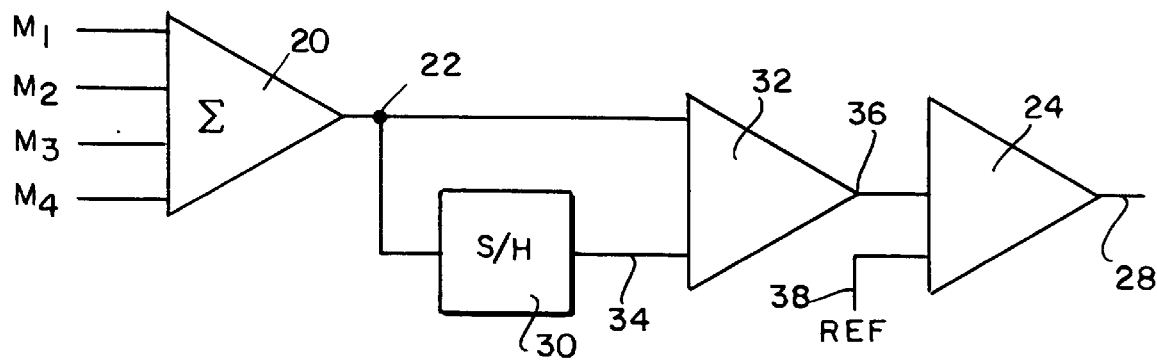
FIG. 4 is a schematic of another analog circuit incorporating the principles of the present invention.

Another implementation of an analog circuit is illustrated in FIG. 4. The output of the summing amplifier 22 is provided into a sample and hold 30. The sample and hold 30 samples and holds the signal when the patient is centered on the support surface. The operation of the sample and hold may be manual or automatic. The output 34 of the sample and hold 30 is a reference weight provided to comparator 32 where it is compared with the sum signal 22. This difference is provided to comparator 24 where it is compared with reference, threshold or boundary signal 38. Reference signal 38 may be the signal 26 of FIG. 3. The output 28 is an indication of whether the difference between a reference weight signal from sample and hold 30 and the present sum 22 is greater than less than a threshold amount 38 and thus whether the patient is or is not in zone 14a. If the output of comparator 32 was an absolute value, the output of comparator 24 would indicate whether the patient is in zone 12 or in zones 14a and 14b.

Figure 5:
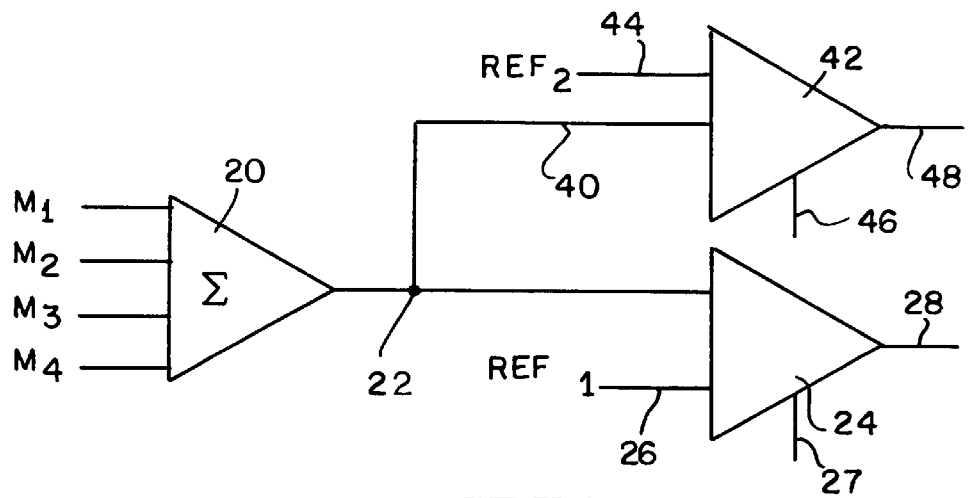
FIG. 5 is a schematic of another analog circuit incorporating the principles of the present invention.

FIG. 5 is a schematic of an analog circuit, similar to FIG. 3, which provides the capability of multiple zones. The summing amplifier 20 provides an output 22 of the weighted signals to the first comparator 24 which has a reference or boundary input 26 for Ref. 1 as well as reference weight or offset input 27. Its output 28 will indicate whether the occupant is in a second zone. A second comparator 42 compares the sum of weighted signal 22 on input 40 against the reference Ref. 2 on input 44. An offset signal 46 is provided to comparator 42. As output 48 indicates whether the occupant is in the third zone defined by reference Ref. 2 and an offset 46.

The offset signals 27 and 46 may be the same reference if it is selected to be the sum signal when the occupant is in the center of the support surface.

FIG. 5 may also operate as a window detector to determine whether the total value from the summer 20 has increased, for example, greater than reference Ref. 1 or has decreased less than Ref. 2. This is achieved by reversing the polarity of the inputs on the comparator 42. Thus, the circuit would indicate whether the patient is in zone 12 or zones 14a or 14b.

It should be noted that the offset or reference weight may be combined with the reference boundary or threshold value and provide as a single input to the comparators. In such a case, the separate input 46 and 27 would not be needed.

Figure 6:
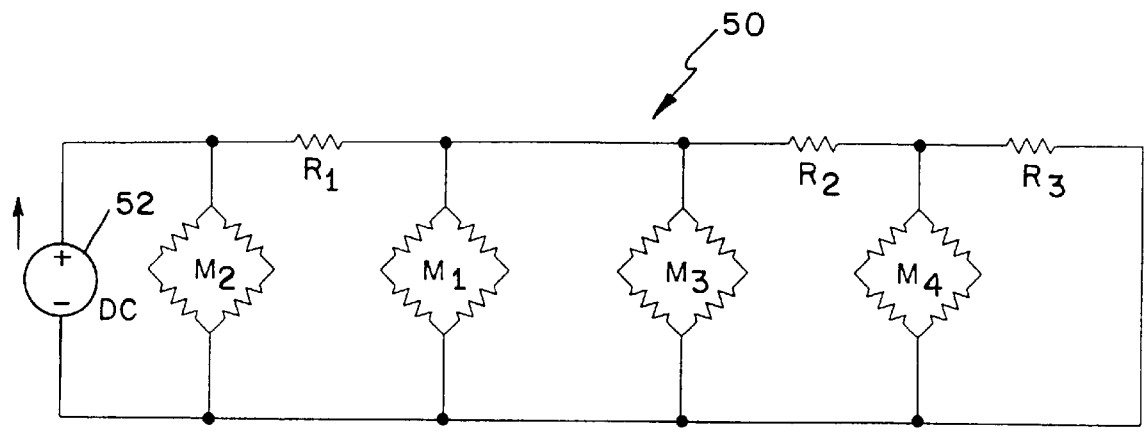
FIG. 6 is a schematic of an analog weighting circuit according to the principles of the present invention.

One method of weighting or modifying the sensitivity of the load cells M1–M4, is illustrated in FIG. 6. This is an analog system wherein a power source 52 is connected to the load sensors M1–M4 illustrated as resistive bridges. The sensor M2 is connected directly to the source 52. The sensors M1 and M3 are connected to the source 52 by a resistor R1. The sensor M4 is connected to the source 52 through resistors R1 and R2. Resistor R3 is the terminal end of the circuit. If R1, R2 and R3 are all equal, the load sensor M2 has twice the weight or sensitivity of M1 and M3 which are equal and M1 and M3 have twice the weight or sensitivity of sensor M4. Thus, the change of the load sensor M1 from the center weight will vary four times as much as that as an M4. Although FIG. 6 shows a weighting of the values or modifying the sensitivity or weight of the sensors by their biasing voltages, an impedance network may be connected to the outputs of the sensors and therefore, their outputs may be weighted analogously.

Figure 7:
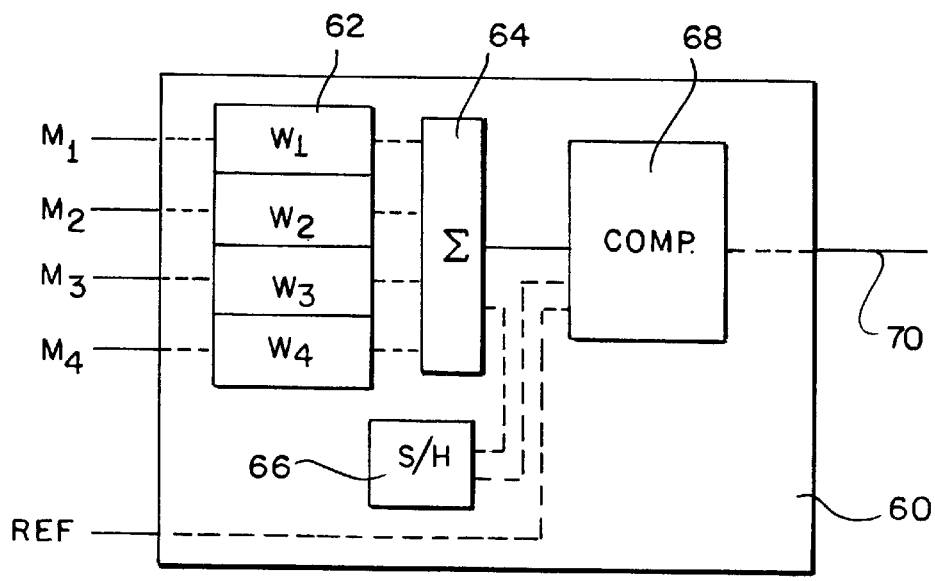
FIG. 7 is a block diagram of a digital microprocessor incorporating the principles of the present invention.

The weighting of the load signals, their summing and comparison to a reference value may also be performed digitally on a computer. As illustrated in FIG. 7, a microprocessor 60 receives its input signals M1–M4 from the load cells. Presignal processing may be performed using the circuit of FIG. 10. The weighting subroutine 62 selects appropriate weighting for all four of the signals. These are provided to a summing subroutine 64. The sum is compared in a comparator subroutine 68 with a reference signal Ref. A sample and hold routine 66 will also provide an input to the comparator 68. The output of the comparison of the sum with the reference and sample and hold is provided as an output 70. This may be an alarm or a quantitative indication of the location of the patient on the support surface.

Figure 8:
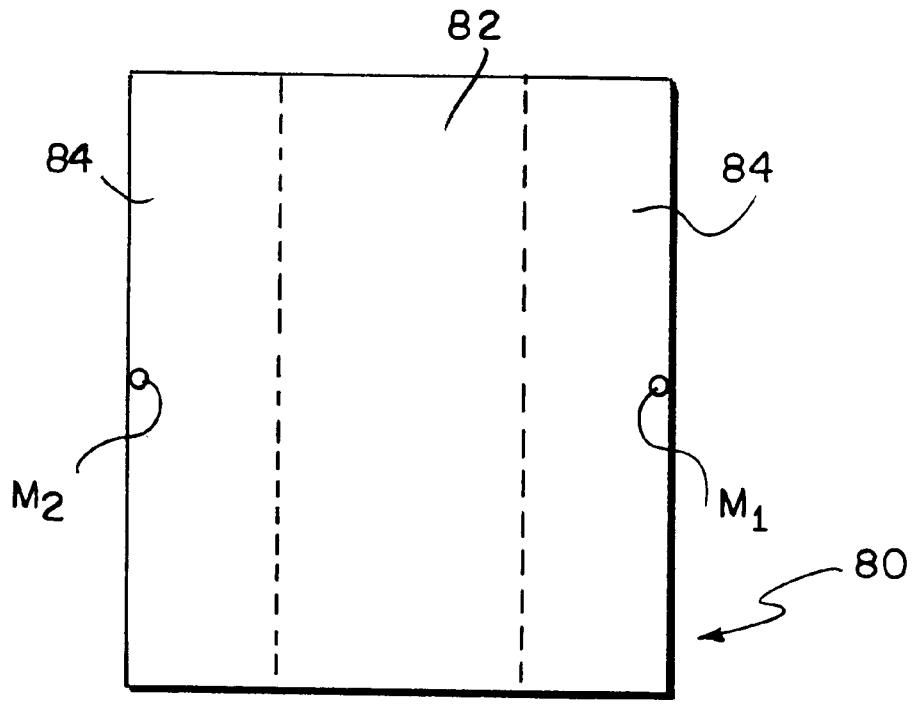
FIG. 8 is a plan view of a load sensing system with two load cells incorporating the principles of the present invention.

Less than all of the sensors, M1–M4 of FIG. 1 may be used. The importance being that any two or more sensors have different weights or sensitivity. Thus, in FIG. 1, sensors M1 and M2 may be used to determine if the patient is moving closer to one of the longitudinal edges of the platform. The simplest system is illustrated in FIG. 8 where sensors M1 and M2 are positioned laterally spaced from each other along the support surface 80. In that M2 has a higher sensitivity or weight than M1, the sum of the signal will vary as occupant moves laterally or across the surface. The present system will provide an indication of whether the patient is in zone 82 or zone 84.

Figure 9:
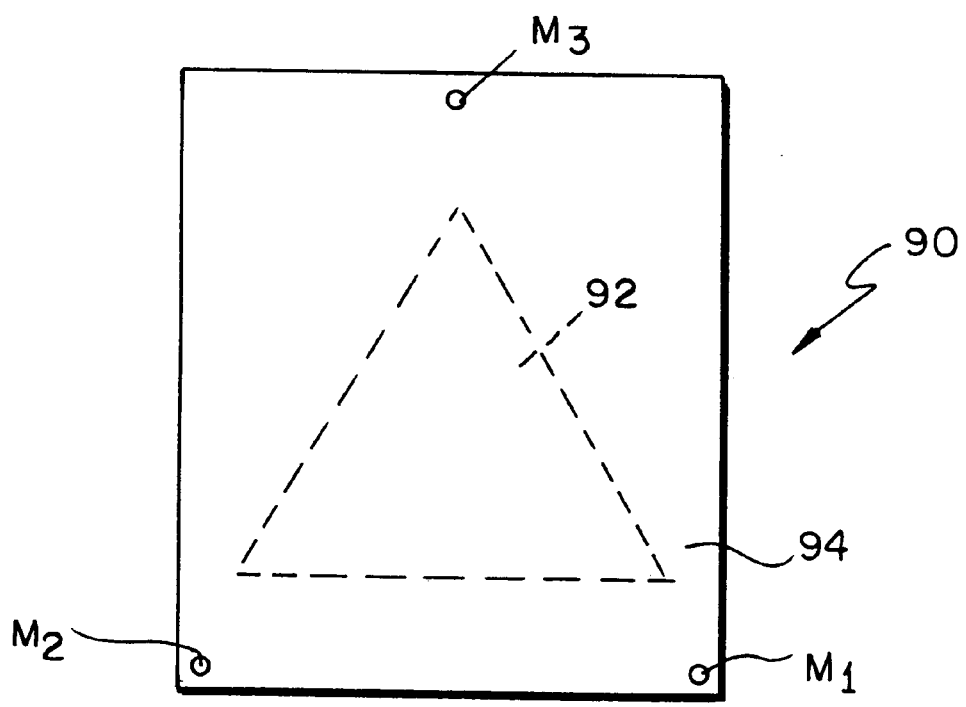
FIG. 9 is a plan view of a load sensing system including three cells incorporating the principles of the present invention.

By adding a third sensor, M3 as illustrated in FIG. 9, it can be determined whether the patient is in center zone 92 or in outer zone 94. Another example of a three point support and support surface would have sensors at the two foot supports for example M1 and M2 of and a third sensor M3 centered at the head support.

It should be noted that if sensors M2 and M4 of FIGS. 1 are used such that the sensor M4 is laterally and longitudinally spaced from M2, any change of the patient with respect to the surface of support surface 10 will reflect in a change of the summed value of the load sensors.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed is:

1. A system for determining the location of a patient on a support, the system comprising:

a patient support surface having longitudinal and lateral edges;

a first and second sensor coupled to the support surface and being at least laterally spaced, the sensors providing first and second load signals respectively;

the first load signal having a first sensitivity greater than a second sensitivity of the second load signal such that a sum of the load signals varies with the location of a patient on the support surface; and a determination circuit receiving the first and second load signals and providing an indication of the location of the patient on the support surface from the comparison of a sum of the load signals to a selected value.

2. A system according to claim 1, wherein the first and second sensors are also longitudinally spaced.

3. A system according to claim 1, including a third sensor coupled to the support surface and longitudinally spaced from the first sensor; the third sensor providing a third load signal; and the third load signal has a third sensitivity less than the first sensitivity.

4. A system according to claim 3, including a fourth sensor coupled to the support surface, longitudinally spaced from the second sensor and laterally spaced the third sensor; the fourth sensor provides a fourth load signal; and the fourth load signal has a fourth sensitivity less than the first sensitivity.

5. A system according to claim 4, wherein the third and fourth sensitivities are greater than the second sensitivity.

6. A system according to claim 5, wherein the third and fourth sensitivities are equal.

7. A system according to claim 3, wherein the third sensitivity is greater than the second sensitivity.

8. A system according to claim 3, wherein the third sensitivity is equal to the second sensitivity.

9. A system according to claim 1, including a signal processing circuit for setting the sensitivity of the load signals.

10. A system according to claim 9, wherein the signal processing circuit includes impedances for setting the sensitivity of the load signals.

11. A system according to claim 9, wherein the signal processing circuit is a programmable signal processor and the sensitivities are set by programming.

12. A system according to claim 11, where the programmable signal processor also includes the determination circuit.

13. A system according to claim 1, wherein the selected value is the sum taken when the patient is substantially centered on the support surface.

14. A system according to claim 1, wherein the selected value is selected based on the weight of the patient.

15. A system according to claim 14, wherein the selected value is selected based on a range of weight in which the weight of the patient lies.

16. A system according to claim 1, wherein the a determination circuit provides an indication of the location of the patient on the support surface from a comparison of a sum of the load signals to a plurality of selected values.

17. A system according to claim 1, wherein the determination circuit provides an indication of the location of the patient on the support surface when the comparison of a sum of the load signals to the selected value is greater than a selected amount.

18. A system according to claim 1, the a determination circuit provides an alarm indication when the location of the patient on the support surface is adjacent the edge of the support surface.

19. A patient support alarm system comprising:
a patient support surface having longitudinal and lateral edges;
a first and second sensor coupled to the support surface and being at least laterally spaced, the sensors providing first and second load signals respectively;
the first load signal having a first sensitivity greater than a second sensitivity of the second load signal such that a sum of the load signals varies with the location of a patient on the support surface; and
an alarm circuit receiving the first and second load signals and providing an alarm indication from a comparison of the sum of the load signals to a selected value.

20. A system according to claim 19, wherein the first and second sensors are also longitudinally spaced.

21. A system according to claim 19, including a third sensor coupled to the support surface and longitudinally spaced from the first sensor; the third sensor providing a third load signal; and the third load signal has a third sensitivity less than the first sensitivity.

22. A system according to claim 21, including a fourth sensor coupled to the support surface, longitudinally spaced from the second sensor and laterally spaced the third sensor; the fourth sensor provides a fourth load signal; and the fourth load signal has a fourth sensitivity less than the first sensitivity.

23. A system according to claim 22, wherein the third and fourth sensitivities are greater than the second sensitivity.

24. A system according to claim 23, wherein the third and fourth sensitivities are equal.

25. A system according to claim 21, wherein the third sensitivity is greater than the second sensitivity.

26. A system according to claim 21, wherein the third sensitivity is equal to the second sensitivity.

27. A system according to claim 19, including a signal processing circuit for setting the sensitivity of the load signals.

28. A system according to claim 27, wherein the signal processing circuit includes impedances for setting the sensitivity of the load signals.

29. A system according to claim 27, wherein the signal processing circuit is a programmable signal processor and the sensitivities are set by programming.

30. A system according to claim 29, where the programmable signal processor also includes the alarm circuit.

31. A system according to claim 19, wherein the selected value is the sum taken when the patient is substantially centered on the support surface.

32. A system according to claim 19, wherein the selected value is selected based on the weight of the patient.

33. A system according to claim 32, wherein the selected value is selected based on a range of weight in which the weight of the patient lies.

34. A system according to claim 19, wherein the alarm circuit provides an alarm indication when the comparison of the sum of the load signals to the selected value is greater than a selected amount.

35. A system according to claim 19, wherein the alarm circuit provides an alarm indication when the sum of the load signals is outside a range of selected values.

36. A method for determining the location of a patient on a support, the support including a patient support surface having longitudinal and lateral edges and a first and second sensor coupled to the support surface and being at least laterally spaced, the sensors providing first and second load signals respectively; the method comprising:
weighting the first load signal to have a first sensitivity and weighting the second load signal to have a second sensitivity less than the first sensitivity such that a sum of the load signals varies with the location of a patient on the support surface;
summing the weighted load signals;
comparing the sum of the load signals to a selected value; and
determining the location of the patent on the support surface from the results of the comparison.

37. A method according to claim 36, including setting the the selected value to the sum taken when the patient is substantially centered on the support surface.

38. A method according to claim 36, including setting the selected value based on the weight of the patient.

39. A method according to claim 38, including setting the selected value based on a range of weight in which the weight of the patient lies.

40. A method according to claim 36, wherein determining the location of the patent on the support surface is from a comparison of a sum of the load signals to a plurality of selected values.

41. A method according to claim 36, wherein determining the location of the patent on the support surface is when the comparison of a sum of the load signals to the selected value is greater than a selected amount.

42. A method according to claim 36, providing an alarm indication when the location of the patient on the support surface is adjacent the edge of the support surface.

43. A method according to claim 36, wherein the first and second sensors are part of a weighing system for the bed; and including weighting load signals from other load sensors of the weighing system to a sensitivity less than the first sensitivity.

* * * * *